United States Patent [19]

Yim et al.

[11] Patent Number: 4,851,220

[45] Date of Patent: Jul. 25, 1989

[54] STABLE OLEAGINOUS GEL

[75] Inventors: Zachary Yim, Paramus; Michael A. Zupon, Madison; Imtiaz A. Chaudry, Denville, all of N.J.

[73] Assignee: Schering Corporation, Kenilworth, N.J.

[21] Appl. No.: 935,479

[22] Filed: Nov. 26, 1986

[51] Int. Cl.$^4$ .................. A61K 45/02; B01J 13/00
[52] U.S. Cl. .................. 424/85.7; 252/309; 252/314; 252/315.4; 514/784; 514/937; 514/944
[58] Field of Search ............ 424/85, 85.7; 514/784, 514/937, 944

[56] References Cited

U.S. PATENT DOCUMENTS

| | | | |
|---|---|---|---|
| 2,792,329 | 5/1957 | Woodard | 252/315.4 X |
| 3,536,816 | 10/1970 | Kellner | 252/315.4 X |
| 4,073,743 | 2/1978 | Midler, Jr. et al. | 252/309 |
| 4,289,690 | 9/1981 | Pestka et al. | 530/351 |
| 4,425,329 | 1/1984 | Tsutsumi et al. | 514/784 X |
| 4,496,537 | 1/1985 | Kwan | 424/85 |
| 4,675,184 | 6/1987 | Hasegawa et al. | 424/85 |

FOREIGN PATENT DOCUMENTS

| | | |
|---|---|---|
| 0032134 | 7/1981 | European Pat. Off. . |
| 0051873 | 5/1982 | European Pat. Off. . |
| 0135171 | 3/1985 | European Pat. Off. ........... 424/85 |

OTHER PUBLICATIONS

Nagata et al., *Nature*, vol. 284, pp. 316-320.
Rubenstein, *Biochimica et Biophysica Acta*, 695 (1982), pp. 5-16.

*Primary Examiner*—Richard D. Lovering
*Attorney, Agent, or Firm*—Anita W. Magatti; James R. Nelson; Stephen I. Miller

[57] ABSTRACT

Stable oleaginous gels comprising water-in-oil emulsions in gels are disclosed. Sustained release injectable pharmaceutical formulations comprising such oleaginous gels are also disclosed, in particular such formulations comprising interferon.

26 Claims, No Drawings

STABLE OLEAGINOUS GEL

SUMMARY OF THE INVENTION

The present invention relates to a stable oleaginous gel comprising a water-in-oil emulsion in a gel, wherein the surfactant for the emulsion is dioctyl sodium sulfosuccinate.

In particular, the invention relates to sustained release injectable pharmaceutical formulations comprising said stable oleaginous gel wherein the active ingredient is preferably a water-soluble biomacromolecule. A preferred water-soluble biomacromolecule is alpha interferon.

BACKGROUND

Emulsions and gels are used in a variety of applications, e.g. cosmetics, foods, insecticides and paints. Similarly, injectable pharmaceutical formulations are well known in the art. See *Remington's Pharmaceutical Sciences*, Mack Publishing Company, Easton, PA, 16th Edition, 1980. Usually such formulations are in the form of dispersions such as colloids, emulsions and suspensions. More recently, sustained release injectable formulations comprising polymers have been used.

Typical sustained release injectable formulations include viscous water-miscible vehicles such as gelatin, water-immiscible vehicles such as oils or oils thickened with such substances as aluminum monostearate, and thixotropic pellets (i.e. formulations which are viscous suspensions on standing, but which became fluid and syringeable when stirred or shaken vigorously, and then reform into viscous "pellets" after injection). Water-in-oil and more often oil-in-water emulsions are used in parenteral products, but usually not in sustained release formulations because such emulsions often present stability problems and may not provide long enough retention time of the active in the formulation, either because the dispersion breaks down or because the dispersion is too soluble in the surrounding body fluids (e.g. blood and lymph systems). Such stability problems are particularly associated with water soluble drugs. Protein drugs present the additional problem of enzymatic degradation in vivo. Practical problems also arise in preparing a formulation fluid enough to be syringeable, but viscous enough to remain in place one injected into the patient.

DETAILED DESCRIPTION

The present invention relates to a stable oleaginous gel, in particular to such a gel suitable for use as a vehicle for sustained release injectable pharmaceutical compositions comprising water-soluble biomacromolecules.

The oleaginous gel is a complex emulsion comprised of two components, a water-in-oil emulsion and a gel. The water-in-oil emulsion component is a slightly viscous emulsion wherein the volumetric ratio of water to oil is in a range of 1:5 to 1:20, preferably 1:10 (i.e., 10% water). Experience has shown that a greater variation in range dramatically changes the viscosity of the emulsion.

The gel component, which acts as the continuous phase into which the water-in-oil emulsion is incorporated, is prepared by adding a gelling agent to an oil. The gelling agent is present at a concentration of 1% to 5%, preferably 2.5% of the weight of the oil in the gelled phase. Any suitable gelling agent may be used, but for parenteral pharmaceutical compositions in particular, gelling agents such as aluminum mono-fatty acid esters are preferred. Examples are aluminum monostearate, aluminum mono-oleate, aluminum monolaurate, aluminum monomyristate and aluminum palmitate, with aluminum monostearate being preferred.

The volumetric ratio of water-in-oil emulsion to gel is 1:0.5 to 1:10, preferably 1.1:1 (i.e., 1:0.9).

Any suitable oil may be used in the emulsion component and to prepare the continuous phase gel, but for pharmaceutical compositions the oils may be any parenterally pharmaceutically acceptable oil such as a vegetable oil, e.g. peanut oil, sesame oil, corn oil, or safflower oil. The preferred oil for both the emulsion and the continuous phase is peanut oil.

The surfactant used to prepare the water-in-oil emulsion, dioctyl sodium sulfosuccinate (DSS), is effective at a very low concentration range, >0.2%, preferably 0.5% by weight of the water present in the emulsion, i.e. >0.01%, preferably 0.025% by weight of the oleaginous gel. DSS has been used as a surfactant in dry cleaning and aerosol products and in stool softening medications, however the concentration used in the instant emulsion is much lower than the 2% by weight used in dry cleaning and the >30 mg per dose used in stool softeners. Furthermore, the use of DSS in parenteral pharmaceutical formulations is previously unreported. It was also found that other conventional surfactants such as Tweens, Spans, Arlacels and modified oils with surface-active properties such as Myglyol and PEG-Castor oil were not sufficiently stable at body temperature (i.e., 37°C.) to be useful in sustained release formulations intended to release the active ingredient over at least a one-week period.

There are several advantages in using the oleaginous gel of this invention to prepare sustained release pharmaceutical formulations. The formulations are easily syringeable through a 25 guage needle as required for intradermal parenteral injection and no special mixing and/or heating is needed as for the thixotropic pellets described above. The oleaginous gel formulation may be prepared in advance and preferably stored under refrigeration, or the formulation may be prepared just prior to use by combining the pre-formed emulsion and the active drug in the solid state, e.g. as a lyophilized power, or the active may be first dissolved in the water used to prepare the water-in-oil emulsion, thus avoiding the need for long-term stability testing for a given active in the emulsion/gel vehicle.

The most significant feature of the oleaginous gel, however, is the length of time during which the sustained release of the active is maintained. Test in guinea pigs indicated release of alpha interferon over twenty days.

While any compatible, pharmacologically useful, parenterally-administerable drug may be used in the instant oleaginous gel parenteral pharmaceutical compositions, the invention is especially useful for water-soluble bio-macromolecules, for example alpha-, beta-, and gamma-interferons, prostaglandins, lymphokines, colony stimulating factors (e.g. GM-CSF), interleukins (e.g. IL-2, IL-3, IL-4), hormones (e.g. adrenocorticotropic hormones (ACTH), lutenizing hormone releasing hormone (LHRH), growth hormones), epidermal growth factor (EGF), tumor necrosis factor, insulin, enkephalins, monoclonal antibodies and soluble vaccines.

Preferred drugs for the instant pharmaceutical compositions are interferons, a family of proteins which exhibit antiviral activity against certain viruses and anti-cancer activity against certain cancers. All types of interferon, i.e. natural or recombinant alpha (leucocyte), beta (fibroblast) and gamma (immune) interferon are contemplated for use in the compositions of this invention, but alpha interferons are preferred. Human alpha interferon is a naturally occuring mixture of at least eleven components including those designated alpha$_1$ and alpha$_2$ interferon, the latter being more preferred in this invention. Human alpha interferon exhibiting biological properties similar to naturally occuring human leucocytes interferon can be made by recombinant methods. Rubenstein, *Biochem. Biophys. Acta.*, 695, 5-16 (1982), Nagata et al., *Nature*, 284, 316-320-(1980), EP No. 32,134 and U.S. Pat. No. 4,289,690 disclose methods for preparing alpha$_2$ interferon. Also included within the scope of this invention are the so-called alpha hybrid interferons wherein fragments of two or more native alpha interferon species are joined (See, for instance EP No. 51,873). Parenteral administration of alpha$_2$ interferon has been reported to be effective in the treatment of several diseases, e.g., viral warts, Kaposi's sarcoma, basal cell carcinoma and multiple myeloma. The effective dose of alpha$_2$ interferon can be easily determined by those skilled in the art.

Additional advantages of the present pharmaceutical formulation for alpha$_2$ interferon in particular are that the formulation is non-denaturing to alpha$_2$ interferon and that the formulation has the requisite physical stability at refrigeration during storage and at body temperature during use.

The following non-limiting examples indicate two methods of preparing injectable pharmaceutical compositions of this invention.

| Alpha interferon (lyophilized) | $1 \times 10^6 - 10 \times 10^8$ IU |
|---|---|
| Water-for-injection for reconstituting | 0.2 ml |
| Dioctyl Sodium Sulfosuccinate | 1 mg |
| Peanut oil for emulsion | 2 ml |
| Peanut oil for gel | 2 ml |
| Aluminum monostearate | 50 mg |

EXAMPLE 1

Mix the aluminum monostearate into the peanut oil for the gel and heat at elevated temperatures to form the gel according to known methods.

Reconstitute the lyophilized alpha interferon with 0.2 ml of water-for-injection containing the dioctyl sodium sulfosuccinate, transfer into the peanut oil for emulsion and mix by vortexing. Transfer the resultant emulsion into the previously prepared gelled peanut oil and mix by vortexing.

| Alpha interferon (lyophilized) | $1 \times 10^6 - 10 \times 10^8$ IU |
|---|---|
| Water-for-injection for reconstituting | 0.2 ml |
| Dioctyl Sodium Sulfosuccinate | 1 mg |
| Peanut oil for emulsion | 2 ml |
| Peanut oil for gel | 2 ml |
| Aluminum monostearate | 50 mg |

EXAMPLE 2

Mix the aluminum monostearate into the peanut oil for the gel and heat at elevated temperatures to form a gel according to well-known methods.

Vortex the water-for-injection containing the dioctyl sodium sulfosuccinate with the peanut oil for the emulsion. Add the lyophilized alpha interferon and mix well by vortexing. Add the gelled peanut oil to the emulsion and mix well by vortexing.

Note that the lyophilized alpha interferon used in the above Examples 1 and 2 comprises a buffer, glycine and human serum albumin added to improve biological stability as described in U.S. Pat. No. 4,496,537, herein incorporated by reference.

The following Example 3 describing a typical preparation of lyophilized alpha interferon.

| Solution for lyophilization | mg/ml |
|---|---|
| Alpha-2 Interferon | $7.5 \times 10^7$ I.U. |
| Sodium Phosphate, Dibasic, Anhydrous, Reagent | 2.27 |
| Sodium Monobasic Phosphate, USP | 0.55 |
| Glycine, USP | 20.0 |
| Albumin, Human, USP | 1.0 |
| Water for Injection, USP q.s. ad | 1.0 ml |

EXAMPLE 3

Charge a portion of water for Injection, USP to a suitable vessel equipped with an agitator. Consecutively charge and dissolve with agitation Sodium Phosphate, Dibasic, Anhydrous Reagent; Monobasic Sodium Phosphate, USP; Glycine, USP; Albumin, Human, USP; and Alpha-$_2$ Interferon. Bring the batch to final volume with Water for Injection, USP.

In a sterile area, aseptically filter the solution into a sterilized vessel through a sterilized 0.2 micron filter which has been washed and tested for integrity. Test the integrity of the filter after filtration.

Aseptically fill the solution into sterilized vials, load filled vials into a sterilized lyophilizer and lyophilize the solution. Aseptically stopper, seal and crimp the vials.

Note that in Examples 1 and 2, the lyophilized interferon is reconstituted with 0.2 ml water, not the 1.0 ml water used to prepare the solution for lyophilization as described in Example 3.

In a preferred aspect of the present invention for the preparation of alpha interferon compositions, the presence of 5-10 mg, preferably 5 mg, human serum albumin per ml of aqueous phase interferon solution is desirable to stabilize the water-in-oil emulsion. The oleaginous gels of this invention comprising alpha interferon may also be prepared by substituting for the lyophilized interferon and water for reconstituting a bulk interferon solution comprising the usual amount of stabilizing ingredients known in the art (e.g. buffers) and human serum albumin as described above.

An additional aspect of the present invention is the preparation of a simplified water-in-oil oleaginous gel by the incorporation of an aqueous phase comprising DSS directly into a gelled oil phase, thereby eliminating the step of preparing a water-in-oil emulsion. The surfactant and gelling agents are present at the same concentration ranges as in the oleginous gel comprising the water-in-oil emulsion. The volume of the aqueous phase similarly represents about the same range as the water-to-total-oil concentration found in the oleaginous gel comprising the water-in-oil emulsion. That is, the surfactant DSS is present at >0.2% by weight of the aqueous phase, the gelling agent is present at 1 to 5% by weight of the oil, and the ratio of the aqueous phase volume to gel volume is 1:10 to 1:40 (i.e., 10 to 2.5% water).

Pharmaceutical compositions comprising said simplified water-in-oil olegenous gel comprise a pharmacologically useful, parenterally administratable water soluble drug in the aqueous phase. Such simiplified water-in-oil oleaginous gels may be prepared in a manner similar to that described in Example 1, i.e., the aqueous phase comprising the DSS is mixed into the gelled oil by vortexing.

We claim:

1. A stable oleaginous gel comprising a water-in-oil emulsion wherein the aqueous phase is the internal phase, the volumetric ratio of water to oil in the water-in-oil emulsion is 1:5 to 1:20 and wherein the surfactant is dioctyl sodium sulfosuccinate present at a concentration of $>0.2\%$ by weight of the aqueous phase of the emulsion, and emulsion being dispersed in a continuous gel phase comprising an oil and a gelling agent, wherein the gelling agent is present at a concentration of 1 to 5% by weight of the oil present in the continuous gel phase, and wherein the volumetric ratio of said emulsion to said continuous gel phase is 1:0.5 to 1:10.

2. A gel of claim 1 wherein the volumetric ratio of water to oil in the water-in-oil emulsion is 1:10.

3. A gel of claim 1 wherein the dioctyl sodium sulfosuccinate is present at a concentration of 0.5% by weight of the aqueous phase of the emulsion.

4. A gel of claim 1 wherein the oil is peanut oil.

5. A gel of claim 1 wherein the gelling agent is aluminum monostearate.

6. A gel of claim 5 wherein the aluminum monostearate is present at a concentration of 2.5% by weight of the oil present in the continuous gel phase.

7. A gel of claim 1 wherein the volumetric ratio of emulsion to continuous gel phase is 1.1 to 1.

8. A gel of claim 1 wherein the oil is peanut oil, the volumetric ratio of water to oil in the water-in-oil emulsion is 1:10, the dioctyl sodium sulfosuccinate is present at a concentration of 0.5% by weight of the water present in the emulsion and the gelling agent is aluminum monostearate present at 2.5% by weight of the oil in the continuous gel phase.

9. A gel of claim 8 wherein the volumetric ratio of emulsion to gel is 1.1 to 1.

10. A sustained release pharmaceutical injectable composition comprising a pharmacologically useful, parenterally administerable, water-soluble drug in an oleaginous gel, wherein the oleaginous gel comprises a water-in-oil emulsion component wherein the oil is a pharmaceutically parenterally acceptable oil, wherein the internal phase of said emulsion is an aqueous solution comprising the drug, wherein the volumetric ratio of water to oil in the water-in-oil emulsion is 1:5 to 1:20 and wherein the surfactant is dioctyl sodium sulfosuccinate, present at a concentration of $>0.2\%$ by weight of the aqueous phase of the emulsion, and wherein said emulsion component is dispersed in a continuous gel phase component comprising a pharmaceutically parenterally acceptable oil and a gelling agent, wherein the gelling agent is present at a concentration of 1 to 5% by weight of the oil present in the continuous gel phase, and wherein the volumetric ratio of said emulsion component to said gel component is 1:0.5 to 1:10.

11. A composition of claim 10 wherein the drug is alpha interferon.

12. A composition of claim 10 wherein the drug is alpha$_2$ interferon.

13. A composition of claim 10 wherein the volumetric ratio of water to oil in the water-in-oil emulsion is 1:10.

14. A composition of claim 10 wherein the dioctyl sodium sulfosuccinate is present at a concentration of 0.5% by weight of the water present in the emulsion.

15. A composition of claim 10 wherein the pharmaceutically parenterally acceptable oil is peanut oil.

16. A composition of claim 10 wherein the gelling agent is aluminum monostearate.

17. A composition of claim 16 wherein the aluminum monostearate is present at a concentration of 2.5% by weight of the oil present in the continuous gel phase.

18. A composition of claim 10 wherein the volumetric ratio of emulsion to continuous gel phase is 1.1 to 1.

19. A composition of claim 10 wherein the pharmaceutically parenterally acceptable oil is peanut oil, the volumetric ratio of water to oil in the water-in-oil emulsion is 1:10, the dioctyl sodium sulfosuccinate is present at a concentration of 0.5% by weight of the aqueous phase of the emulsion and the gelling agent is aluminum monostearate present at 2.5% by weight of the oil in the continuous gel phase.

20. A composition of claim 19 wherein the volumetric ratio of emulsion to gel is 1.1 to 1.

21. A composition of claim 20 wherein the drug is alpha$_2$ interferon.

22. A composition of claim 21 comprising $5 \times 10^6$ to $5 \times 10^9$ IU alpha interferon/ml aqueous phase.

23. A composition of claim 20 wherein the aqueous phase comprises $5 \times 10^6$ to $5 \times 10^9$ IU alpha interferon/ml, 25 to 750 mg glycine/ml, 5–10 mg human serum albumin/ml and a compatible buffer to maintain the pH of the solution within the range of about 6.5 to 8.0.

24. A composition of claim 23 comprising 100 mg glycine/ml, 5 mg human serum albumin/ml, and wherein the buffer is a sodium phosphate buffer.

25. A stable oleaginous gel comprising a water-in-oil emulsion wherein the aqueous phase is the internal phase, the volumeric ratio of water to oil is 1:10 to 1:40 and wherein the surfactant is dioctyl sodium sulfosuccinate present at a concentration of $>0.2\%$ by weight of the aqueous phase, said aqueous phase being dispersed in a continuous gel phase comprising an oil and a gelling agent, wherein the gelling agent is present at a concentration of 1 to 5% by weight of the oil present in the continuous gel phase.

26. A sustained release pharmaceutical injectable composition comprising a pharmacologically useful, parenterally administerable, water-soluble drug in an oleaginous gel, wherein the oleaginous gel comprises a water-in-oil emulsion wherein the internal phase of said emulsion is an aqueous solution comprising the drug, wherein the volumetric ratio of water to oil is 1:10 to 1:40 and wherein the surfactant is dioctyl sodium sulfosuccinate, present at a concentration of $>0.2\%$ by weight of the aqueous phase, and wherein the aqueous phase is dispersed in a continuous gel phase comprising a pharmaceutically parenterally acceptable oil and a gelling agent, wherein the gelling agent is present at a concentration of 1 to 5% by weight of the oil.

* * * * *